(12) United States Patent
Bruszewski et al.

(10) Patent No.: US 8,197,475 B2
(45) Date of Patent: Jun. 12, 2012

(54) METHOD AND STRUCTURE FOR AMELIORATING SIDE-EFFECTS OF PERFORMING IN SITU FENESTRATION USING A PLASMA RF CATHETER

(75) Inventors: Walter Bruszewski, Guerneville, CA (US); Trevor Greenan, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1121 days.

(21) Appl. No.: 12/049,522

(22) Filed: Mar. 17, 2008

(65) Prior Publication Data
US 2009/0234348 A1 Sep. 17, 2009

(51) Int. Cl.
*A61B 18/18* (2006.01)
*A61B 18/04* (2006.01)

(52) U.S. Cl. ............... 606/41; 606/34; 623/1.32

(58) Field of Classification Search ........... 606/32–48; 623/1.11, 1.35
See application file for complete search history.

(56) References Cited

U.S. PATENT DOCUMENTS

| | | | |
|---|---|---|---|
| 5,617,878 A | 4/1997 | Taheri | |
| 5,916,213 A | 6/1999 | Haissaguerre et al. | |
| 5,984,907 A | 11/1999 | McGee et al. | |
| 6,210,406 B1* | 4/2001 | Webster | 606/41 |
| 6,955,657 B1 | 10/2005 | Webler | |
| 2002/0007181 A1* | 1/2002 | Zikorus et al. | 606/41 |
| 2002/0035361 A1* | 3/2002 | Houser et al. | 606/15 |
| 2003/0191512 A1* | 10/2003 | Laufer et al. | 607/101 |
| 2004/0193150 A1 | 9/2004 | Sharkey et al. | |
| 2007/0010784 A1 | 1/2007 | Soykan | |
| 2007/0219576 A1 | 9/2007 | Cangialosi | |
| 2008/0108987 A1 | 5/2008 | Bruszewski et al. | |
| 2008/0125773 A1 | 5/2008 | Yeh et al. | |
| 2008/0208121 A1* | 8/2008 | Youssef et al. | 604/114 |

FOREIGN PATENT DOCUMENTS

DE 102006006052 A1 10/2006
TW M312294 U 5/2007
* cited by examiner

*Primary Examiner* — Michael Peffley
*Assistant Examiner* — Khadijeh Vahdat (57) ABSTRACT

When a main stent-graft is placed in a vessel of a patient and a branch vessel is blocked by the main stent-graft, a RF plasma catheter is used to cut out a portion of the graft cloth of the main-stent graft adjacent to an ostium of the branch vessel to be perfused. To ameliorate possible adverse effects associated with the use of the RF plasma catheter, e.g., creation of coagulum, (desiccated, coagulated blood) or perhaps a cut stent strut, a special process using saline flushing, a novel RF plasma catheter with an insulated tip, or a combination of the two is used.

15 Claims, 13 Drawing Sheets

METHOD AND STRUCTURE FOR AMELIORATING SIDE-EFFECTS OF PERFORMING IN SITU FENESTRATION USING A PLASMA RF CATHETER

BACKGROUND OF THE INVENTION

1. Field of the Invention

The present invention relates generally to use of stent-grafts, and more particularly to fenestration of a stent-graft in situ.

2. Description of Related Art

A conventional main (vessel) stent-graft typically includes a radially expandable reinforcement structure, formed from a plurality of annular stent rings, and a cylindrically shaped layer of graft material, sometimes called graft cloth, defining a lumen, to which the stent rings are coupled. The stent rings includes straight portions that are referred to as struts. Main stent-grafts are well known for use in tubular shaped human vessels.

To illustrate, endovascular aneurysmal exclusion is a method of using a main stent-graft to exclude pressurized fluid flow from the interior of an aneurysm. This reduces the risk of rupture of the aneurysm and the associated risk of mortality.

Main stent-grafts with custom side openings are sometimes fabricated to accommodate particular vessel geometries of each individual patient. Specifically, as the location of branch vessels emanating from a main vessel, e.g., having the aneurysm, varies from patient to patient, main stent-grafts to treat such configurations are fabricated with side openings customized to match the position of the branch vessels of the particular patient. However, custom fabrication of main stent-grafts is relatively expensive and time consuming.

To avoid custom fabrication of main stent-grafts, side openings in the main stent-graft may be formed in situ. Illustratively, the main stent-graft is placed in the main vessel, e.g., the aorta, to exclude an aneurysm. Fenestrations may be made in situ to correspond to positions of the adjacent branch vessels. See U.S. Pat. No. 5,617,878 of Taheri.

The graft material of the main stent-graft is pierced with a needle at the ostium of a branch vessel, e.g., the renal artery, emanating from the main vessel. A fenestration is typically initiated with a small needle perforation of the graft material. The perforation must be enlarged with a conical dilator.

For example, an expandable balloon is inserted in the needle perforation in the graft material of the main stent-graft. However, considerable force is required to expand the balloon and tear the graft material.

The application of such a considerable force is difficult to control and thus leads to unpredictability in the tear of the graft material or other complications. Further, the branch stent-graft tends to propagate the rent (a split or tear) in the graft material over time. Also, the edge of the rent fractured the branch stent-graft depending upon the particular application. Finally, the edge of the rent was a fray of loose fibers of the graft material, which tended to unwind over time.

SUMMARY OF THE INVENTION

A method includes using a radio frequency (RF) plasma catheter in a branch vessel which reduces adverse side effects during the in situ fenestration of a main-stent graft in a main vessel. The RF plasma catheter is used to create a fenestration in situ in a main stent graft when the branch vessel is blocked or covered by the main stent graft.

A step contributing to reducing side effects includes injecting a pulse of a flush solution before, during and after the fenestration to create a micro environment of the flush solution about an RF electrode of the RF plasma catheter. A step contribution to reducing side effects also includes using an insulator in the RF plasma catheter to maintain a separation of the RF electrode from a strut of the main stent graft to prevent damage to the strut during creation of the fenestration.

The injecting of a pulse of flush solution starts a flow of a flush solution through the RF plasma catheter. The fenestration is created in the stent graft cloth by applying power to the RF electrode of the RF plasma catheter at a time t1 after the starting of the flow. The flow of the flush solution is maintained while applying power. The flow of the flush solution is terminated at a time t2 after the application of power is stopped. The flow of flush solution washes blood away from the RF electrode and thereby reduces coagulum formed by the heating of blood associated with the application of power to the RF electrode.

A radio frequency (RF) plasma catheter assembly includes a center liner bounding a lumen. A RF electrode is coupled to the center liner at a distal end of the center liner. The RF electrode bounds a lumen aligned to provide a flow path from the lumen of the center liner through the RF electrode. A source of a flush solution is coupled to the center liner. An outer insulator is mounted about the RF electrode. A circumferential outer edge surface of the outer insulator comprises a portion of an outer circumferential edge surface of the RF catheter assembly.

An inner insulator is mounted between the center liner and the RF electrode. The inner insulator bounds a lumen aligned to provide a flow path from the lumen of the center liner to the lumen of the RF electrode.

In one implementation, the RF electrode includes a convex exterior edge surface. In another implementation, the RF electrode includes a concave exterior edge surface.

DETAILED DESCRIPTION

In one implementation according to the present invention, when a main stent-graft is placed in a vessel of a patient and a branch vessel is blocked by the main stent-graft, a RF plasma catheter is used to cut out a portion of the graft cloth of the main-stent graft adjacent to an ostium of the branch vessel to be perfused. To ameliorate possible adverse effects associated with the use of the RF plasma catheter, e.g., creation of coagulum, (desiccated, coagulated blood) or perhaps a cut stent strut, a special process, a novel RF plasma catheter, or a combination of the two is used.

To facilitate the widespread use of the RF plasma catheter (which nearly eliminates the unpredictability associated with the need to apply large forces to initiate and mechanically expand an in situ fenestration in the prior art) to provide in situ fenestration of a main stent-graft, potential side-effects of the fenestration are ameliorated. In the step of Configure Fenestration Catheter For Reducing Adverse Side Effects step 110 of process 100 (FIG. 1), a radio-frequency (RF) plasma catheter is configured to include at least one configuration of (1) a RF plasma catheter electrode bounded by an insulator and (2) a pulsed flush capability. The next step is, in Install Stent Graft step 120, a main stent graft is placed in a main vessel of a patient using well known techniques.

Figure 1:
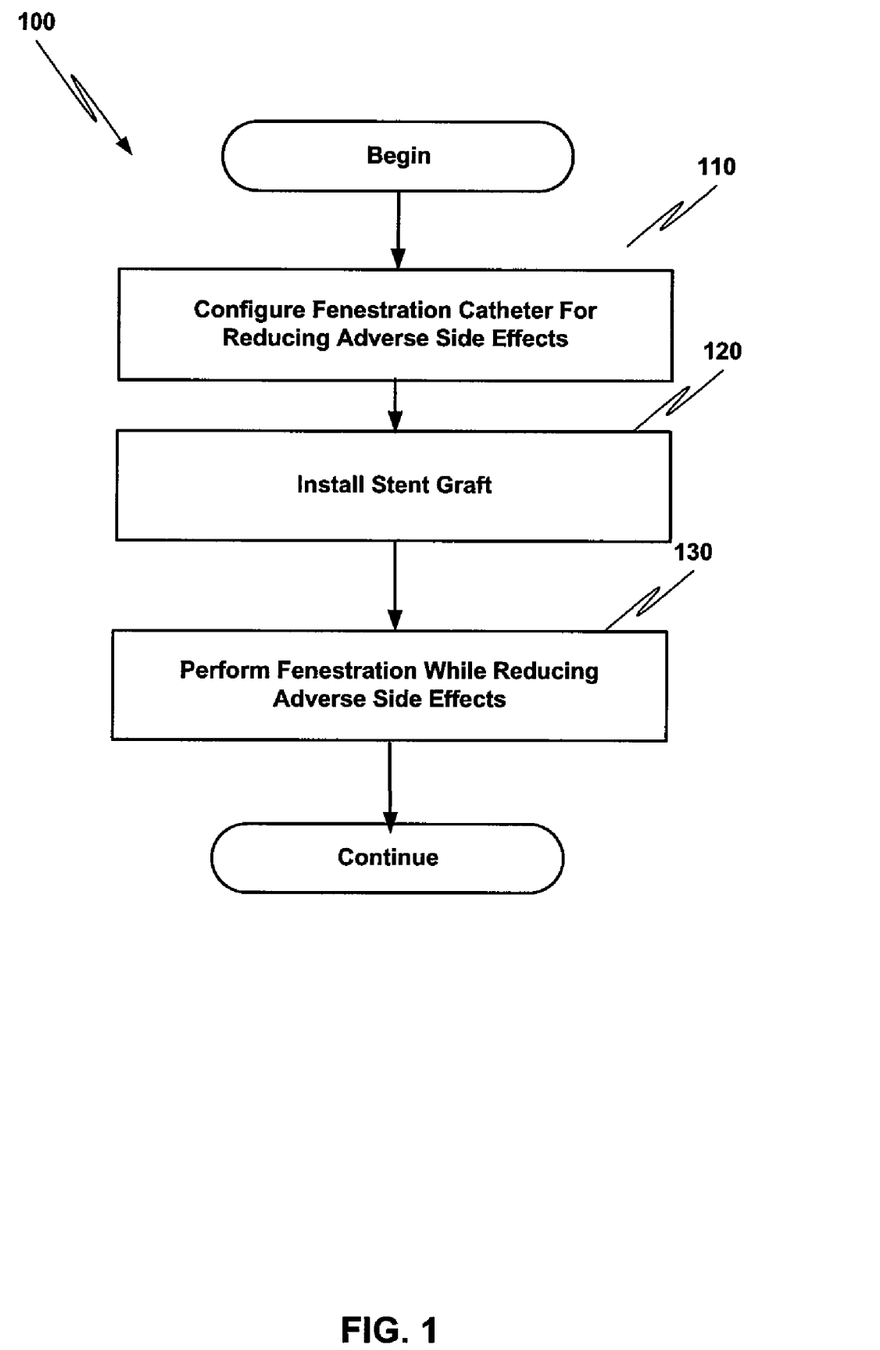
FIG. 1 is a process flow diagram for one implementation of the method according to this invention.

In the final step of, Perform Fenestration While Reducing Adverse Side Effects step 130 cuts a portion out of the graft cloth of the main-stent graft adjacent to an ostium of the branch vessel to be perfused using the RF plasma catheter from step 110. After step 130 is completed, the branch graft placement process continues as is known in the prior art and so is not described herein.

If the pulsed flush capability is used in step 130, a pulse of flush solution is injected through the RF plasma catheter so that blood is washed away from both the site of the fenestration and the RF plasma catheter electrode. If the RF plasma catheter electrode is bounded by an outer insulator, the stent struts are shielded from the plasma and the heat generated by the plasma. Thus, the possibility of cutting a main stent graft strut is reduced. Alternatively, the RF plasma catheter can include both the pulsed flush capability and the RF plasma catheter electrode circumferentially bounded by an outer insulator, which reduces both coagulum and the possibility of damaging a stent strut.

A more detailed example of process 100 using the pulsed flush capability is presented in describing FIGS. 2A, 2B, 3A, 3B, 3C, and 4 to 6. In this example, a method 400 (FIG. 4) is used. The sequence of steps (processes) in method 400 is illustrative of one of several possibilities. In view of this disclosure, those of skill in the art can modify the sequence as appropriate for a particular procedure while still achieving the advantages of ameliorating side effects of using the RF plasma catheter for fenestration in situ.

Figure 4:
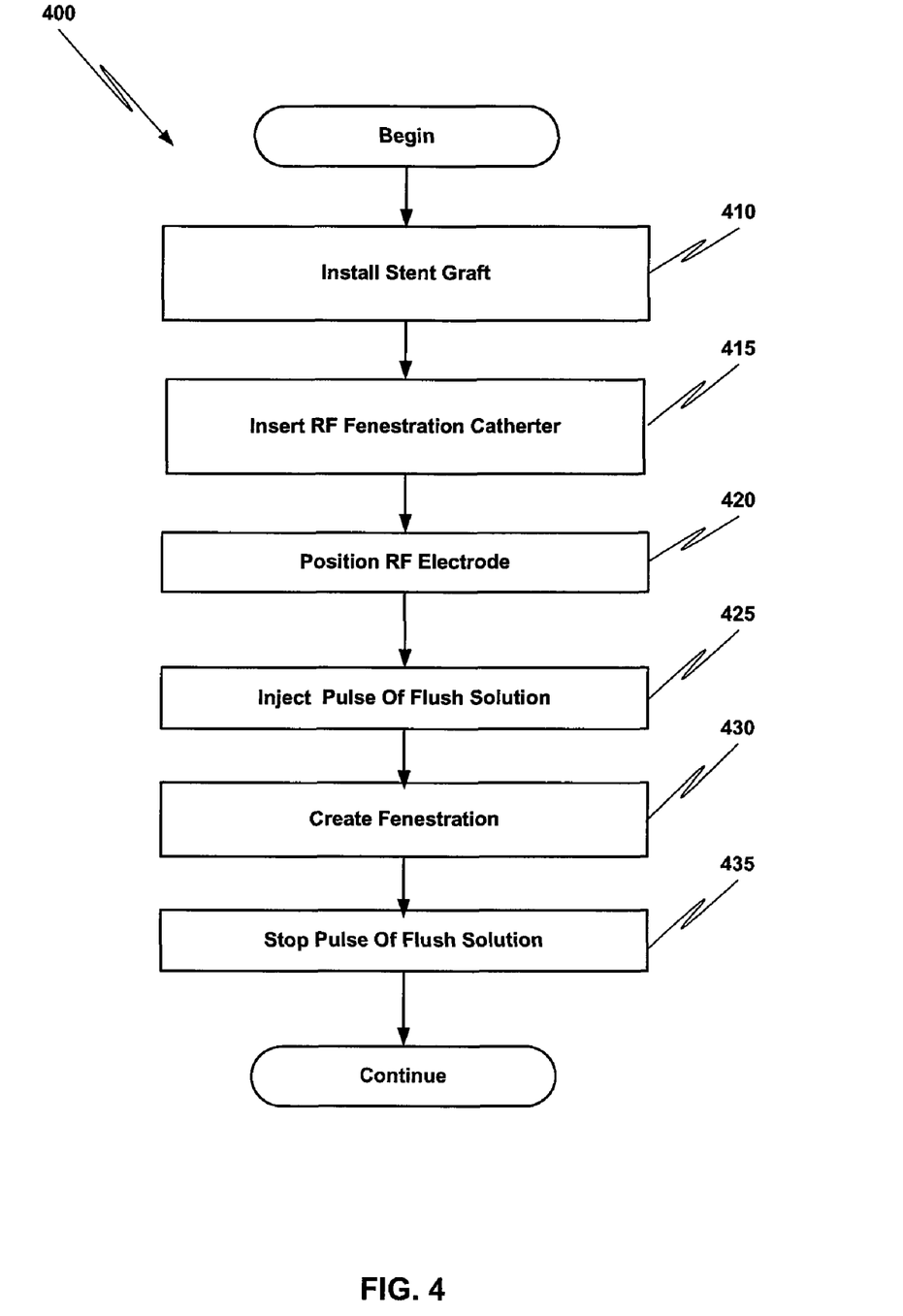
FIG. 4 is a more detailed process flow chart associated with the implementation illustrated in FIGS. 2A, 2C, and 3A to 3C.

In install stent graft step 410, a main stent graft 230 (FIG. 2A) is placed in a vessel 210 of a patient—vessels such as the aorta and the branches such as innominate, left common carotid, and left subclavian arteries, but could be the arteries of the descending aorta as well. Vessel 210 includes an aneurysm 211. Main stent graft 230 includes a plurality of stent struts including stent strut 231 and stent graft cloth 232. The construction of main stent graft 230 is known to those of skill in the art.

Figure 2A:
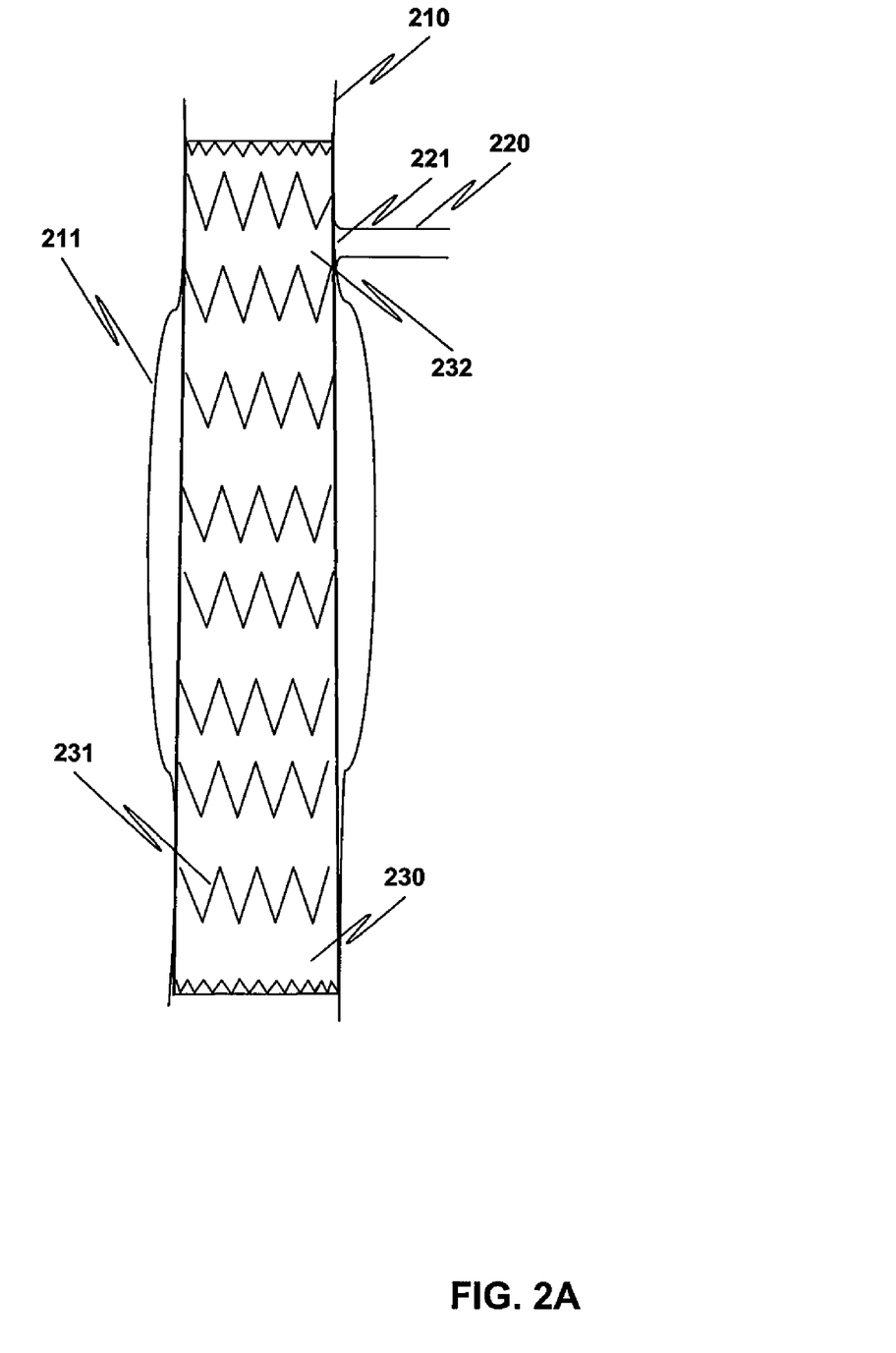
FIG. 2A is an illustration of a main stent graft in a main vessel where the main stent graft blocks profusion of a branch vessel.
Figure 2B:
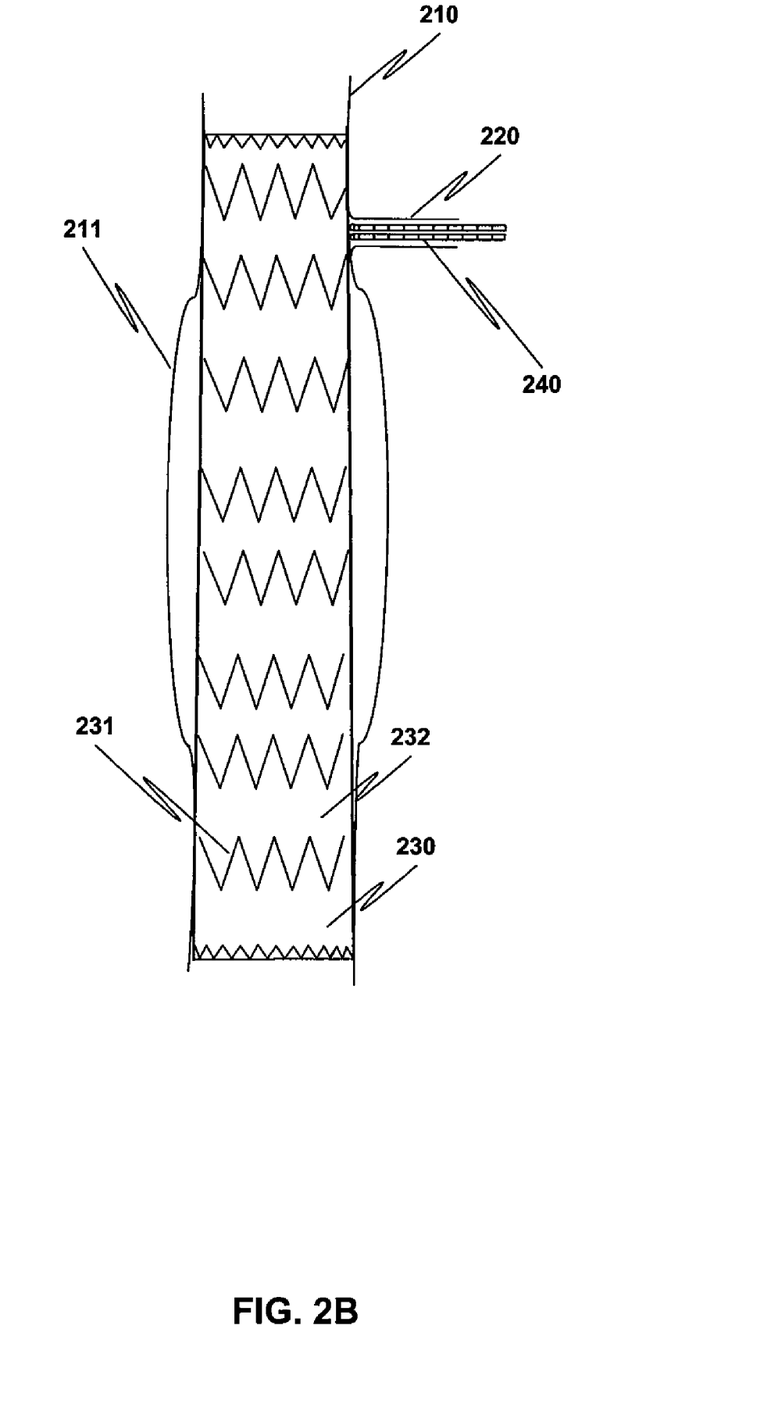
FIG. 2B is an illustration of an implementation of the RF plasma catheter being positioned in the branch vessel.

Main stent graft 230 blocks an ostium 221 of branch vessel 220. Thus, an opening in main stent graft 230 is needed to allow perfusion of branch vessel 220.

In Insert RF Fenestration Catheter step 415 (FIG. 4), a RF plasma catheter 240 (FIG. 2B) with a flush capability is inserted in the patient and positioned in branch vessel 220 (See FIGS. 2B and 3A), using conventional techniques.

Figure 3A:
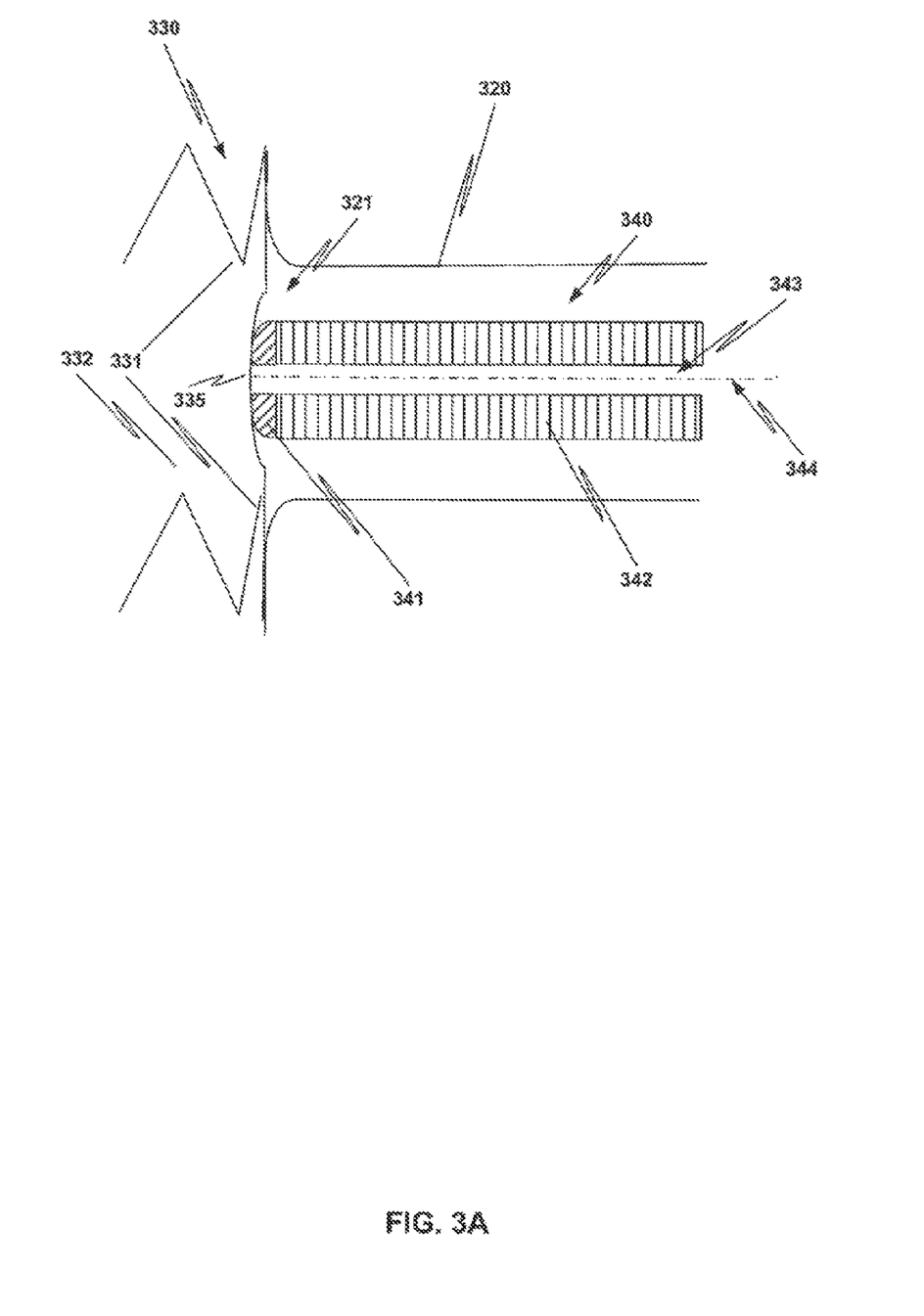
FIG. 3A is a more detailed illustration of the position of the RF plasma catheter of FIG. 2B.
Figure 3B:
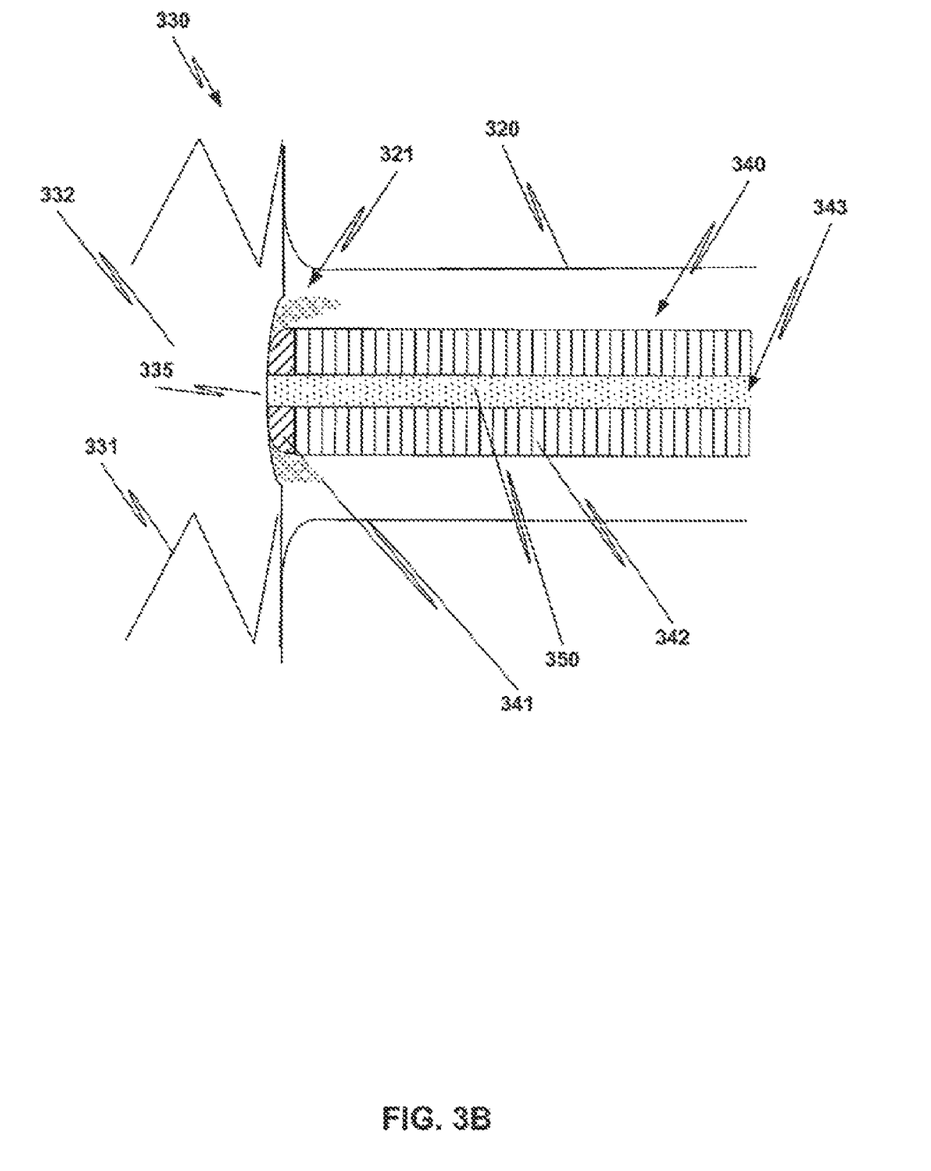
FIG. 3B illustrates the flow of the flush solution for the configuration of FIG. 3A after the flow of flush solution is started.

In Position RF Electrode step 420, a RF plasma catheter electrode, sometimes referred to as RF electrode, of RF plasma catheter 240 is positioned adjacent and contacting stent graft cloth 332, as shown in more detail in FIG. 3A, between two struts 331. RF electrode 341 is placed against stent graft cloth 332 so that an indentation 335 is created in stent graft cloth 332 in this example. This is illustrative only and is not intended to limit the use of such a device to such indentations. In general, it has been observed that best fenestration results are obtained when RF electrode 341 is in contact with stent graft cloth 332.

RF plasma catheter 340 includes an annular body 342 bounding a channel 343, sometimes called lumen 343, which is coupled to a source of a flush solution. In this example, channel 343 is oriented along and about a longitudinal axis 344 of RF plasma catheter 340. RF electrode 341 also bounds a lumen that is aligned to provide a flow path from lumen 343 through said RF electrode 341.

RF electrode 341 of RF plasma catheter 340 is coupled to a power supply similar to those used for cautery devices. Generally, RF electrode 341 is formed of an electrically conductive material. In one example, RF electrode 341 is formed of a super elastic memory material, e.g., nitinol. In another example, electrode 341 is formed of stainless steel. In other examples, RF electrode 341 is formed of a radiopaque material to aid in visualization of RF electrode 341 using an imaging process, for example, so that RF electrode 341 is visible using x-rays. Illustrative examples of radiopaque materials from which RF electrode 341 can be formed include platinum-iridium, tantalum, gold, and stainless steel.

In this embodiment, an electrode (not shown) is coupled to the patient, typically a pad of electrically conducting saline hydrogel is affixed to the patient that is also coupled to the power supply. This electrode is called the ground or common electrode and is electrically connected to the patient, for example, using an electrically conductive gel.

The particular configuration of RF plasma catheter 340 with RF electrode 341 is not essential in this example so long as the RF plasma catheter is capable of creating an opening in graft cloth 332 using a plasma in conjunction with the pulsed flush of this example. RF plasma catheters suitable for use in method 400 are described more completely below, as well as in copending and commonly assigned, U.S. patent application Ser. No. 11/557,204, entitled "Cutting Radio Frequency Catheter for Creating Fenestrations in Graft Cloth" of Walter Bruszewski and Patrick MacAulay filed on Nov. 7, 2006.

After the RF electrode, i.e., RF electrode 341, is in position, a flush solution 350 (FIG. 3B) is started through channel 343 in Inject Pulse Of Flush Solution step 425. The flow rate and pressure of flush solution 350 is chosen so that any blood in the vicinity is washed away from the region about RF electrode 341 in ostium 321 and from indentation 335 about RF electrode 341. Those of skill in art will appreciate that the flow of flush solution 350 could also be started before RF electrode 341 is in position, e.g., in contact with graft cloth 332.

Figure 3C:
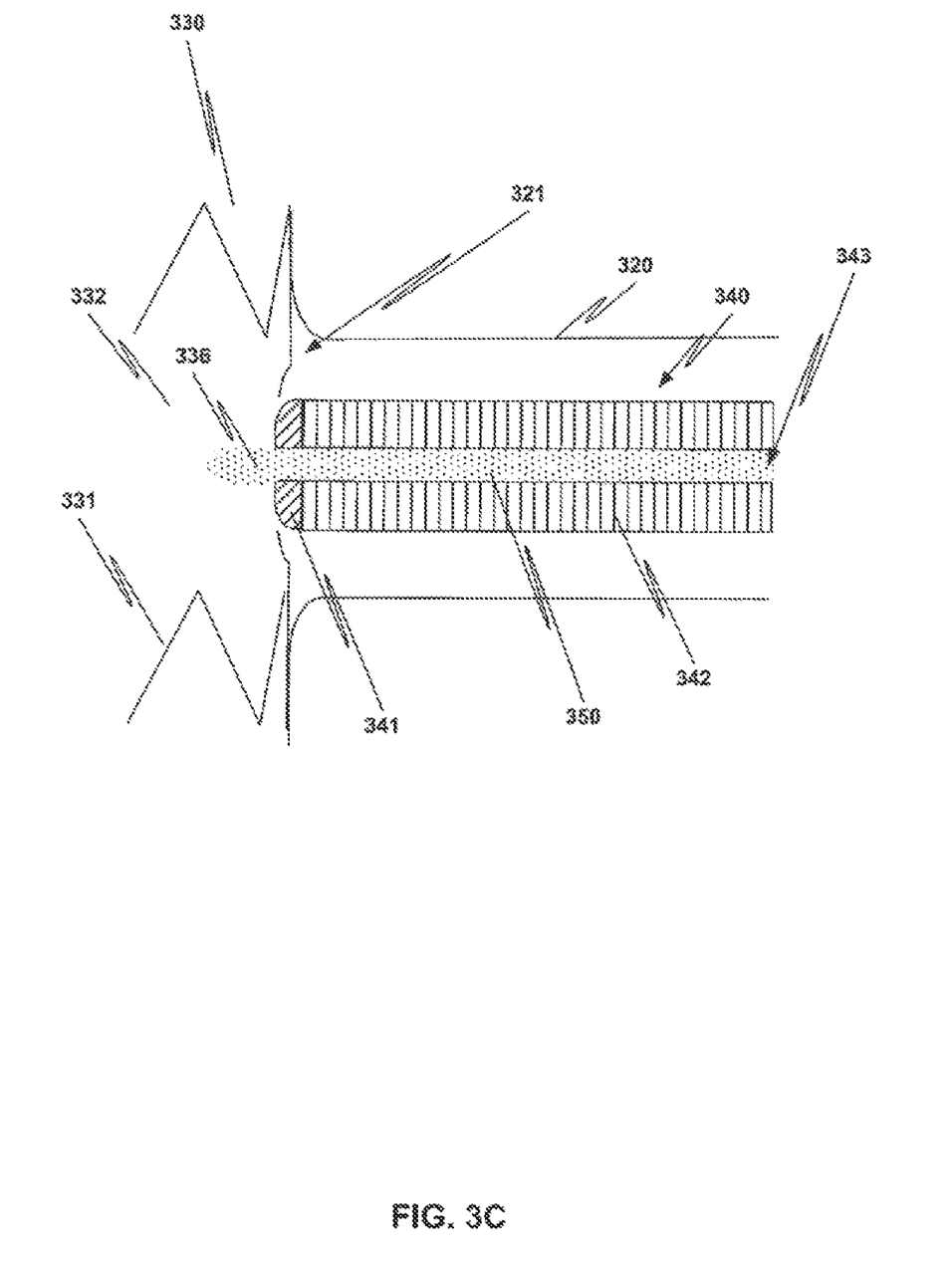
FIG. 3C illustrates the flow of the flush solution for the configuration of FIG. 3B after the applying of power to the RF electrode is started.

While the flow of flush solution 350 is maintained, power is applied to RF electrode 341 in create fenestration step 430. A plasma is created that results in a hole being cut in graft cloth 332, i.e., creates fenestration 336 (FIG. 3C). The heat from the plasma fuses the edges of fenestration 336. As illustrated in FIG. 3C, flush solution 350 flows through fenestration 336 into the interior volume of main stent graft 330.

Following creation of fenestration 336, flow of flush solution 350 is continued until the flow is stopped in Stop Pulse Of Flush Solution step 435. The remaining processes used in possibly installing a stent graft in branch vessel 320 and removing RF plasma catheter 340 from the patient are similar to those previously known and so are not described here further to avoid detracting from the disclosure.

Thus, in this example, immediately prior to, during and immediately after the fenestration, any blood in the vicinity of the RF electrode is washed away from that vicinity and blocked from the fenestration site by the continuing flow of the flush solution. An example of timing for a pulse of flush solution 510 with respect to timing of RF pulse 520 to RF electrode 341 is presented in FIG. 5.

Figure 5:
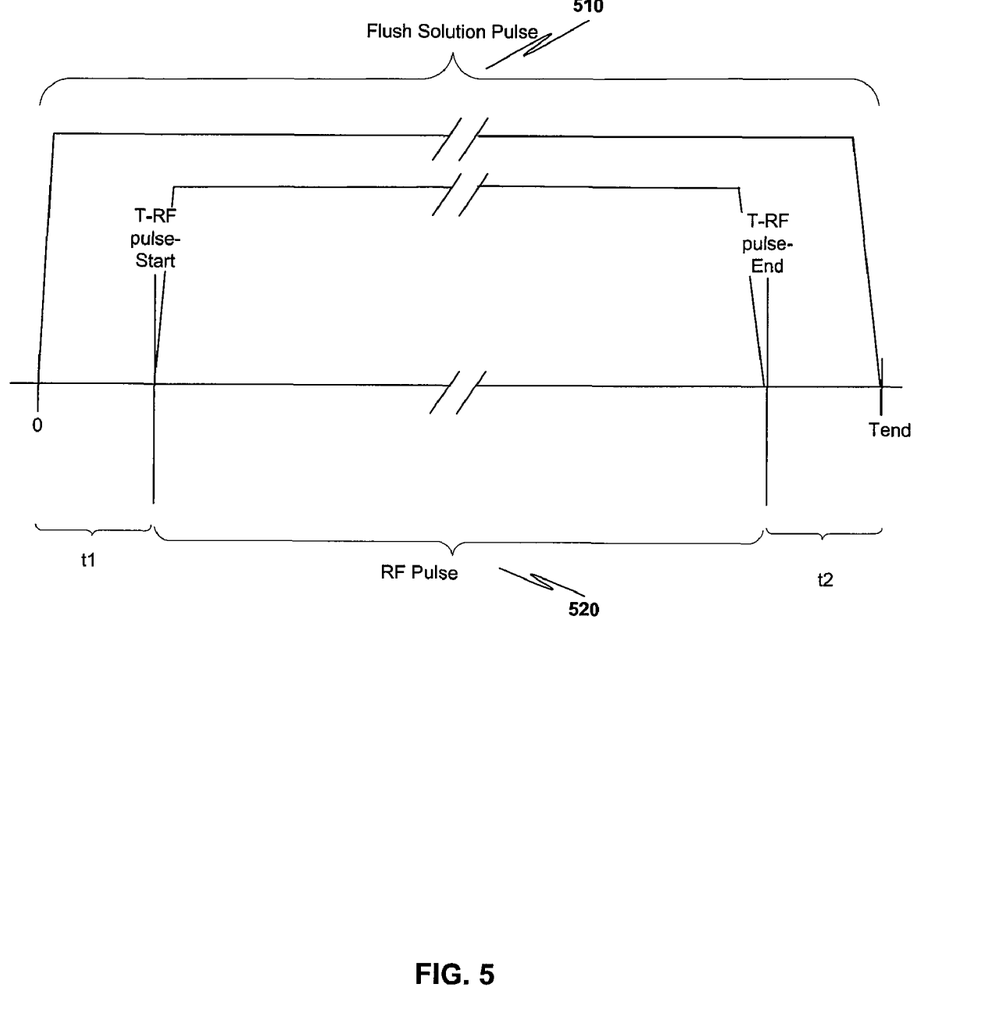
FIG. 5 is an example of timing for a pulse of flush solution with respect to timing of a RF pulse to the RF electrode.

At time 0, step 425 starts a flush solution pulse 510. After time period t1, at time T-RF pulse Start, power is applied to RF electrode 341 in step 430 and power is maintained until time T-RF pulse End. After time period t2 from time T-RF pulse End, step 435 stops flush solution flow at time Tend. The vertical displacements in FIG. 5 have no meaning and are not intended to specify any relationship between the two pulses. Similarly, FIG. 5 is not intended to limit the option which might be considered for any specific pulse rise and fall times.

The initial edge of the pulse of flush solution 510 starts to dilute the blood near RF electrode and the continued flow washes blood away from the fenestration site and away from RF electrode 341. The continuing flow associated with pulse 510 prevents blood from reaching the fenestration site and RF electrode 341. Thus, the pulse of flush solution 510 washes blood away and blocks blood from the fenestration site and from RF electrode 341 while RF pulse 520 is active. The flush solution conducts the RF energy.

Since pulse of flush solution 510 isolates the fenestration site from blood flow, the RF plasma catheter cuts the graft cloth in a microenvironment of the flush solution instead of blood. Thus, the environment is essentially the flush solution. Consequently, the potential to generate coagulum is reduced, if not eliminated, because blood has been removed from the microenvironment in which the plasma is created to cut the graft cloth. Because it is known that conductivity of a typical flush solution is significantly higher than blood, a power efficiency of RF fenestration will be increased. With higher efficiency a shorter plasma discharge or a lower-power discharge will be possible. This decrease in discharge duration and heat will also diminish coagulum formation.

In one implementation, time period t1 and time period t2 have a same duration, for example, 50 msec (milliseconds). In this implementation, the duration of RF pulse 520 is 1000 msec and so the duration of flush solution pulse 510 is 1100 msec. Alternatively, in another implementation, time period t1 and time period t2 can have different durations.

Also dual balloons could be used to block blood follow through the main stent graft, use a dual core RF plasma catheter via the auxiliary vessel, inject saline in one core of catheter, open other core of catheter to use as saline drain, do the cutting, continue to inject saline and in this way flush all the coagulum, small particles of graft cloth etc. out and then unblock flow through stent graft.

Figure 6:
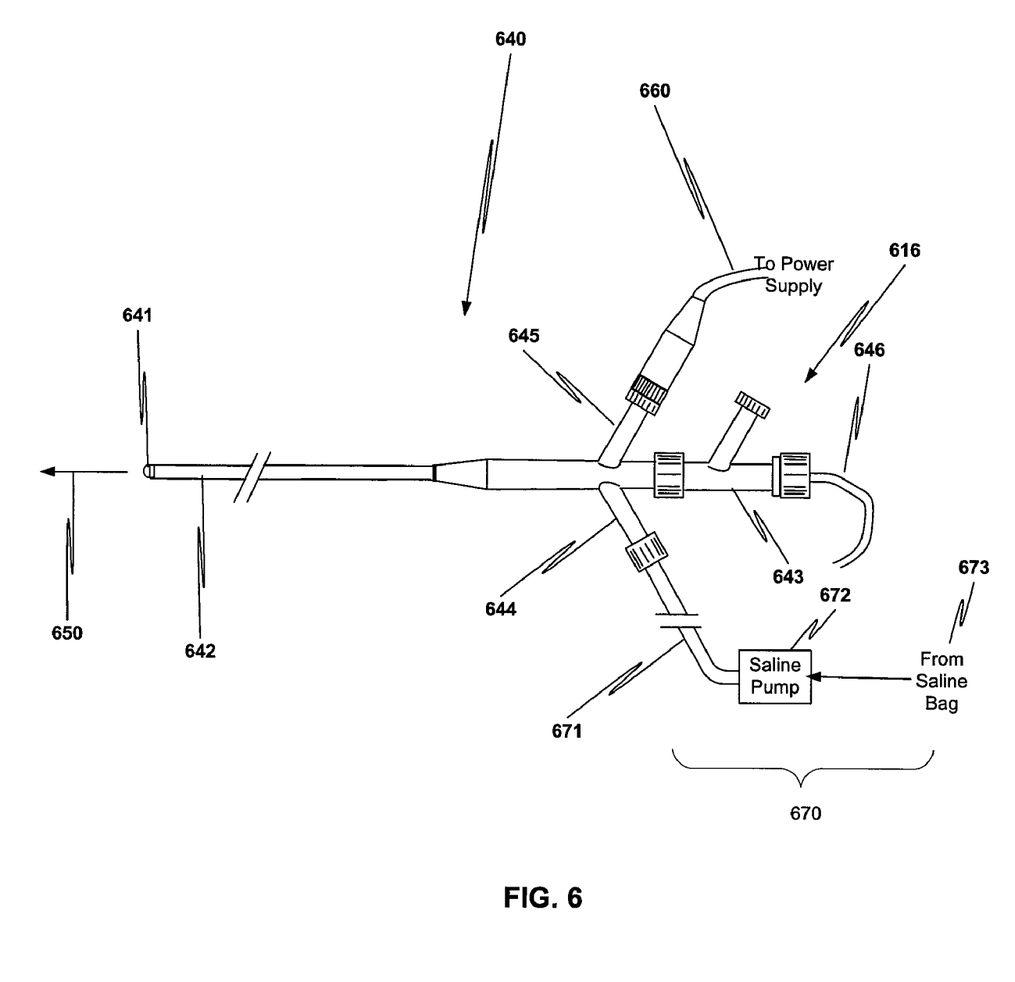
FIG. 6 is a schematic view of one example of a saline-assisted RF plasma electrode fenestration catheter assembly.

FIG. 6 is a schematic view of one example of a saline-assisted RF plasma electrode fenestration catheter assembly 640, sometimes referred to as RF plasma catheter 640, suitable for use in the methods described above. RF plasma catheter 640 includes RF electrode 641 at a proximal end of RF plasma catheter 640 and an operator's handle 616 includes three ports 643, 644, and 645 at a proximal end of RF plasma catheter 640. As used herein, the distal end of RF plasma catheter 640 is referenced with respect to operator's handle 616.

As described more completely below, RF electrode 641 is electrically connected to an RF conductor (not shown) that in turn is connected to a receptacle in port 645. Thus, the RF conductor extends from the distal end to the proximal end of RF plasma catheter 640

In one implementation, the RF conductor is a metal wire such as a copper, steel, NiTi, or stainless steel wire, or is formed of the same material as RF electrode 641. The RF conductor is welded or soldered to RF electrode 641 and is wound around an annular center liner (not shown). The annular center liner is coupled to RF electrode 641 so that a continuous channel for flow of flush solution 650 is available. The wire can have a covering that is an insulator is, for example, a silicone elastomer, polyamide, or polyurethane.

A piece or pieces of thermoplastic tubing are placed over the center liner and RF conductor and heat shrunk to form catheter shaft 642 that extends from RF electrode 641 to handle 616. The techniques for forming catheter shaft 642 with a center liner covered with thermoplastic tubing are equivalent to those used in the prior art and so are known to those of skill in the art in view of this description. For example, techniques for providing power and flow channels through a catheter shaft are described in U.S. Pat. No. 5,916,213, entitled "Systems and Methods for Tissue Mapping and Ablation," of Haissaguerre et al, issued on Jun. 29, 1999, which is incorporated herein by reference as evidence of the level of skill in the art.

The RF conductor is electrically connected to a RF power supply (not shown) through port 645 via RF power line 660. In this example, RF power line 660 is terminated by a banana jack that plugs into the receptacle in port 645. During use, the RF power supply supplies RF power via RF power line 660 to the RF conductor and thus to RF electrode 641.

Illustratively, the RF power supply operates in the 200-500 kHz frequency range.

As another example, the power output of RF power supply is in the range of 50 to 300 watts and is capable of providing 100 to 300 watts/sec. For example, the RF power supply is a Valleylab Cautery RF generator (Model Force FXTM Electrosurgical Generator manufactured by Valleylab—5720 Longbow Dr., Boulder, Colo.) although any one of a number of RF generators can be used. Although particular frequency and power output ranges are provided, these are illustrative only.

Port 644 is coupled to a source of flush solution such as a bag of saline. Typically one would use 0.9% NaCl; possible alternatives are balanced salt solutions, such as Ringers and Hanks BSS—it must be an isotonic, physiological saline. Specifically, output flow 673 of the bag of saline is connected to an input port of saline pump 672. The output port of saline pump 672 is connected to a saline supply tube 671 that in turn is connected to saline inflow port 644. Port 644 is configured to provide the saline to the inner channel, sometimes called lumen, of catheter shaft 642.

In one implementation, saline pump 672 is a roller pump. In another implementation, saline pump 672 is a positive displacement pump. Saline pump 672 provides 50 to 100 ml/min flow with a pressure ranging between 2 and 15 atmospheres. The saline from saline bag 673 and saline pump 672 provide a source of flush solution 670.

Port 643 is a Touhy-Borst adapter allows passage of the guidewire 646 which guides the catheter to the fenestration site, the guidewire can be pulled back during fenestration. In another example, guidewire 646 includes a catching structure (corkscrew like shaped structure) at a distal end of guidewire 646. As described in copending U.S. patent application Ser. No. 11/557,204, the catching structure catches the flap of graft material cut from the graft material by RF electrode 641.

A guidewire 646, e.g., a 0.035 inch guidewire, extends out the guidewire lumen of port 643. The guidewire 646 extends through the length of catheter shaft 642 in the channel described above. While no problem with electrical coupling with the guidewire has been detected, a guidewire may include a dielectric coating or be formed of a dielectric material or be enclosed in a guiding catheter.

In another example to ameliorate adverse side effects of using a RF plasma catheter 740 (FIG. 7) for in situ fenestration, a RF plasma catheter electrode 741 of RF plasma catheter 740 is bounded by an outer insulator 745. Outer insulator 745 is a high temperature electrical insulator in this implementation. Here, high temperature means that outer insulator 745 can be used in proximity to high temperature, because outer insulator 745 is a poor conductor of heat and so acts as an insulator from the high temperature as well as an electrical insulator.

Figure 7:
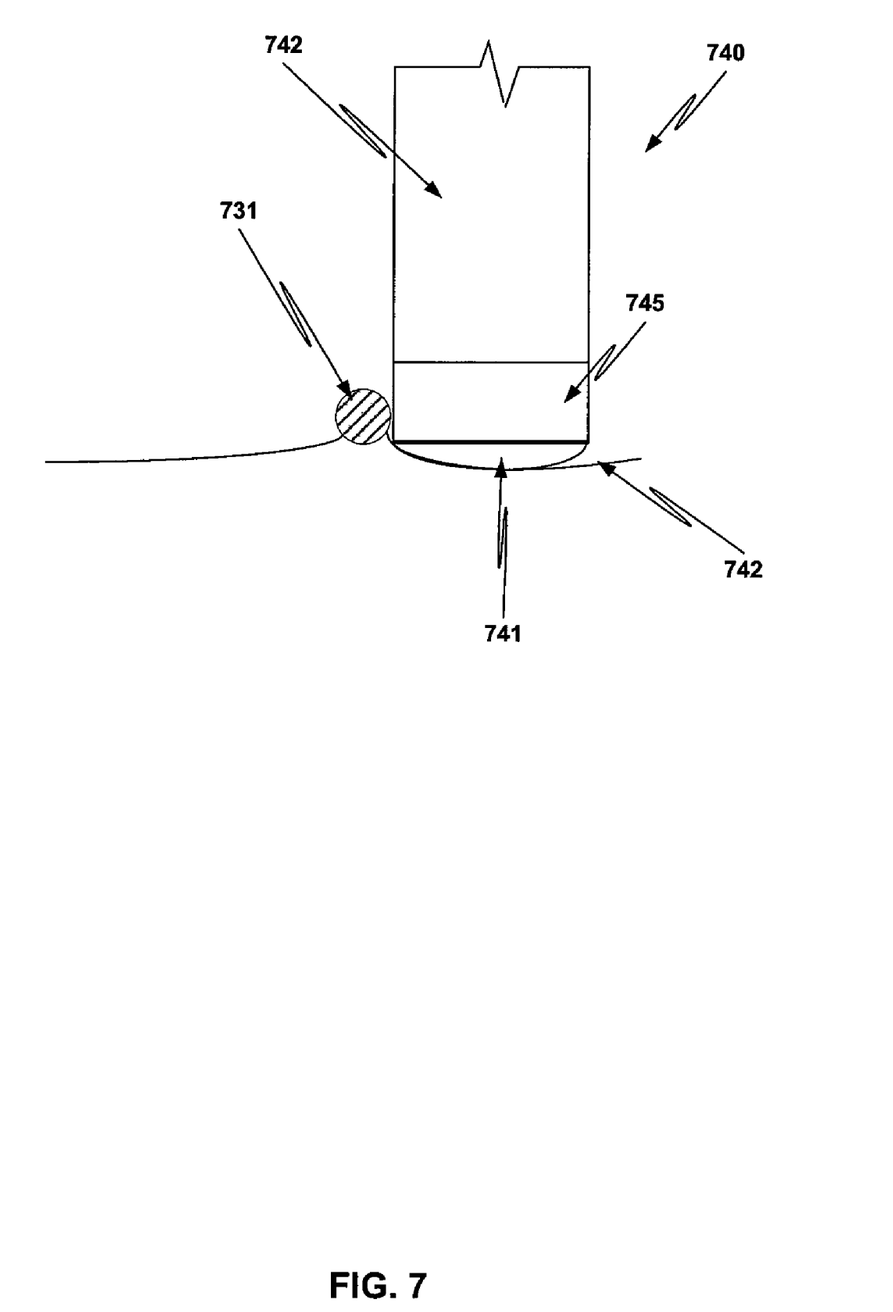
FIG. 7 is an illustration of an implementation of the RF plasma catheter that includes an outer insulation for maintaining a separation between a stent strut and a RF electrode of the RF plasma catheter.

Outer insulator 745 causes RF electrode 741 to be separated from a main stent graft strut 731 while RF electrode 741 positively contacts, e.g., depresses, main stent graft cloth 742 during fenestration. This separation effectively shields stent strut 731 from the plasma created during fenestration and from the heat generated by the plasma. Thus, the potential for RF plasma catheter 740 to inadvertently cut strut 731 is greatly reduced, if not eliminated.

Figure 8:
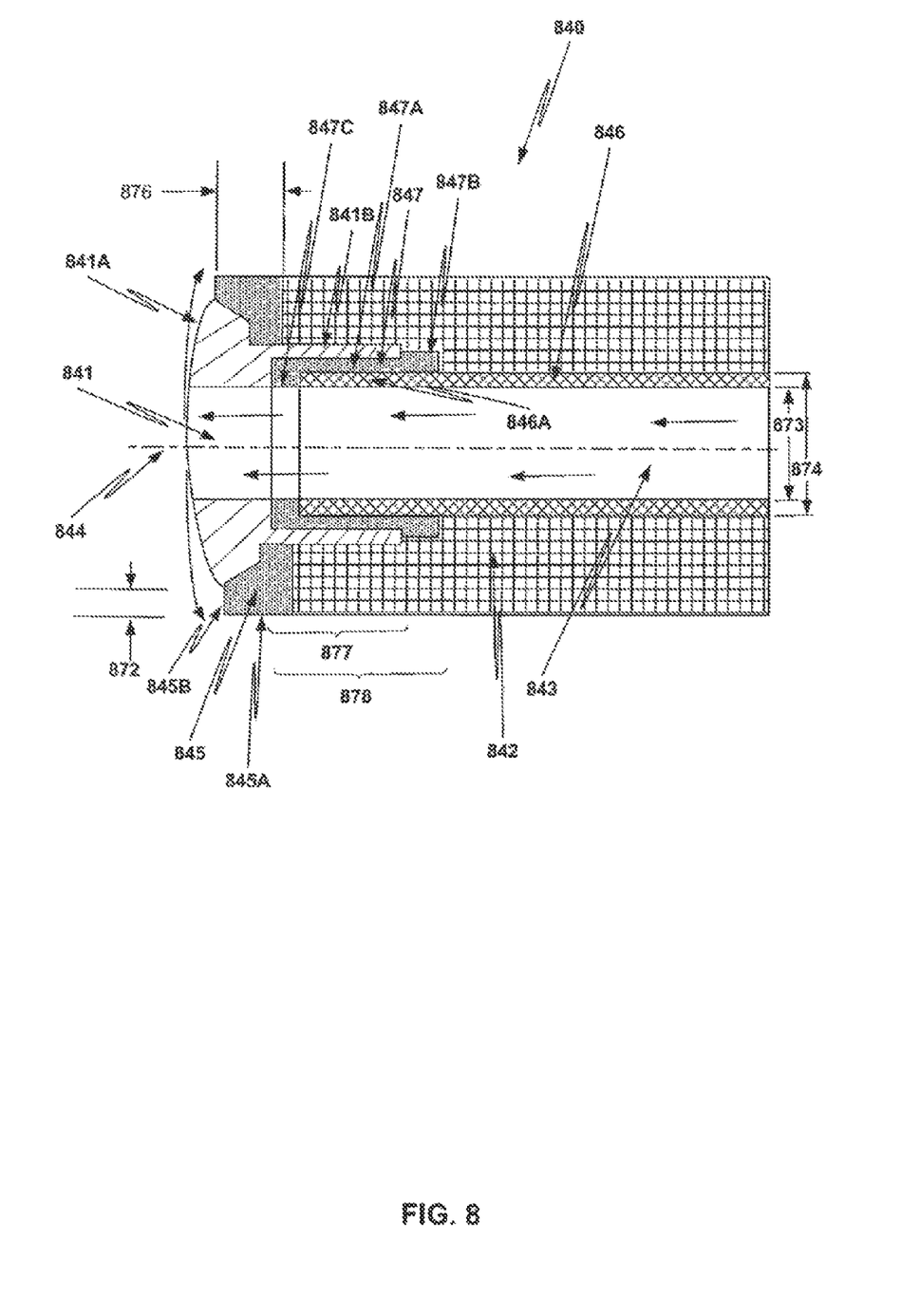
FIG. 8 is a cross-sectional view of one implementation of a RF plasma catheter that includes a RF electrode with a convex exterior edge surface and an outer insulator.

FIG. 8 is a cross sectional view of a portion of one implementation of a RF plasma catheter 840 that includes an outer insulator 845 which will maintain separation between a stent strut and the RF electrode. In this implementation, RF plasma catheter 840 also includes RF electrode 841, inner insulator 847, center liner 846, and catheter shaft body 842.

Center liner 846 is a cylindrical annulus having an inner diameter 873 and an outer diameter 874. An inner circumferential edge surface of center lining 846 has diameter 873 and bounds channel 843, sometimes called lumen 843. Inner diameter 873 can range from 0.018 in) to 0.042 in) and in this implementation is 0.039 in). Outer diameter 874 can range from 0.022 in) to 0.046 in) and in this implementation is 0.043 in). Center liner 846 can be formed from a polymer tube such as polymide, stainless steel wire braid reinforced polyimide, polyamide, PEEK, or HDPE.

Distal end 846A of center liner 846 is mounted within inner insulator 847. Inner insulator 847 is made from a material that functions as a high temperature electrical insulator. For example, an ultra high temperature machineable ceramic is used to form inner insulator 847. The ultra high temperature machineable ceramic has the following properties: Max temp of 3100° F., thermal conductivity of 181 Btu/hr.xin./sq. ft. One ceramic suitable for use, Very High Temperature Non-porous High-Alumina Ceramics can be obtained from McMaster-Carr Industrial Supply, Santa Fe Springs, Calif.

The exact shape and size of inner insulator 847 is selected to insulate center liner 846 from the heat deposited in RF electrode 841 during fenestration so that the structural and physical integrity of center liner 846 is not compromised by that heat. In this example, inner insulator 847 includes an annular wall 847A with an exterior lip 847B about one end of annular wall 847A and an interior lip 847C about an opposite end of annular wall 847A.

An inner diameter of annular wall 847A is selected based on outer diameter 874 of center liner 846 so that inner insulator 847 is affixed to center liner 846. Typically inner insulator 847 is bonded to outer liner 846 using high temperature epoxy adhesive. In this example, the outer diameter of annular wall 847A is 0.060 in. However, this value is illustrative only and in one implementation, the outer diameter is selected from a range of 0.040 in to 0.100 in.

An outer diameter of exterior lip 847B and a length of exterior lip 847B along longitudinal axis 844 are selected to isolate center liner 846 from any heat conducted from annular section 841B of RF electrode 841. The lip having length of 0.020-0.025 in. and a diameter of 0.070-0.080 in. An inner diameter of interior lip 847B is diameter 873. A length of interior lip 847B along longitudinal axis 844 is selected to isolate center liner 846 from any heat conducted from RF electrode 841. In this implementation, inner insulator 847 has a length 878 along longitudinal axis 844, which is 0.020-0.025 in.

Outer insulator 845, as described above, is a high temperature electrical insulator. In this embodiment, the general shape of outer insulator 845 is annular with an inner edge surface modified as illustrated in FIG. 8 to facilitate affixing both outer insulator 845 and RF electrode 841 to RF plasma catheter 840 while insulating a stent strut adjacent to outer circumferential edge surface 845A from the heat and plasma associated with RF electrode 841. Outer insulator 845 is made from the same material as inner insulator 847.

In this implementation, outer circumferential edge surface 845A has a length 876 along longitudinal axis of 0.010-0.030 in. However, this value is illustrative only. Exterior separation edge surface 845B has a length 872 approximately transverse to longitudinal axis 844 of 0.010-0.015 in. However, this value is illustrative only and in one implementation, the length is selected from a range of 0.13 mm (0.005 in) to 0.020 in. The inner diameter of outer insulator 845 is dependent on the thickness of annular wall 841B of RF electrode 841.

Figure 9:
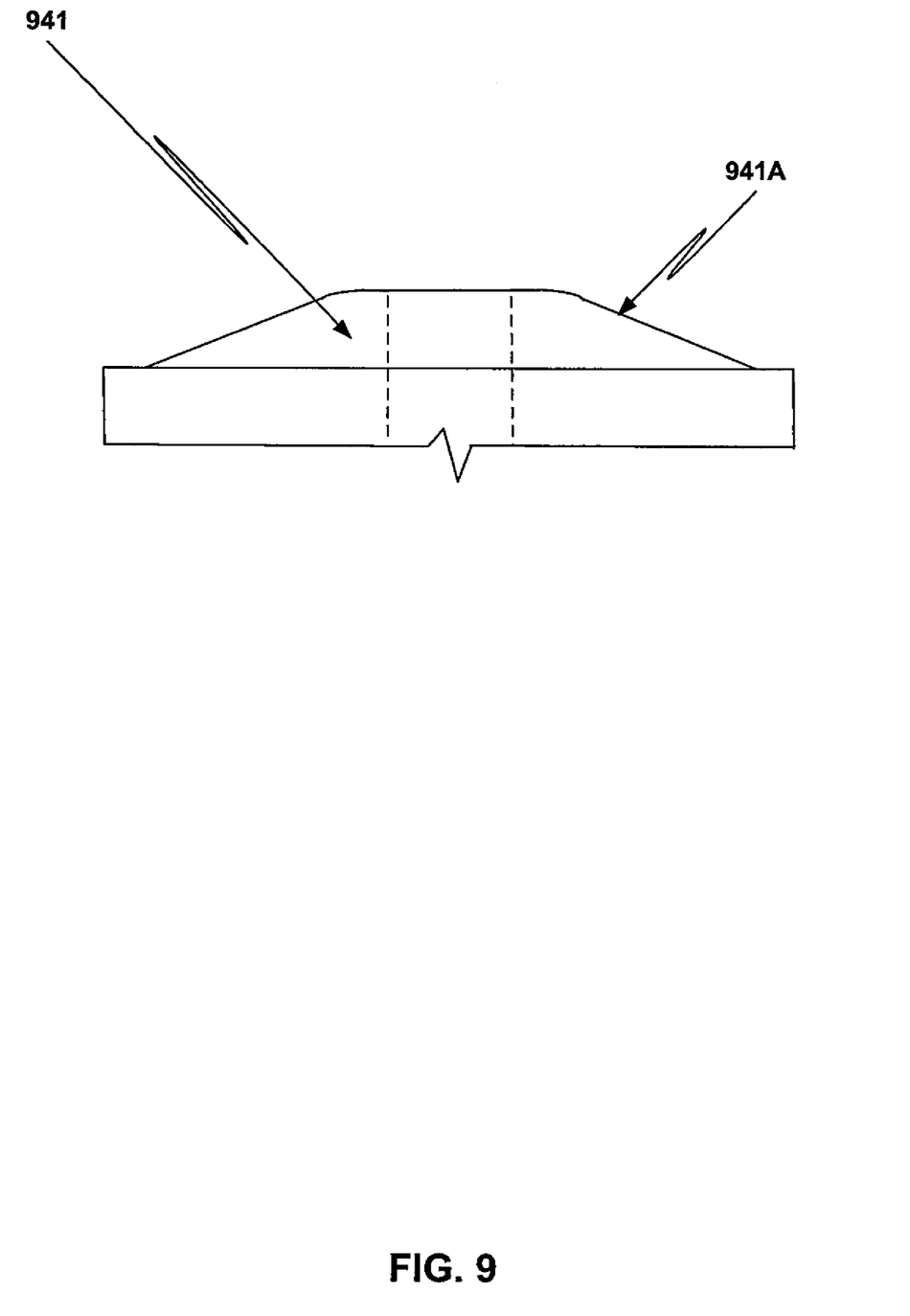
FIG. 9 is an illustration of convex exterior edge surface suitable for the RF electrode of FIG. 8.

RF electrode 841 has a convex exterior edge surface 841A, which in this implementation is a smooth arc. However, this illustrative only and is not intended to limit possible embodiments to this specific shape. FIG. 9 is illustrates an alternative convex exterior edge surface 941A for RF electrode 941. RF electrode 841 has an inner circumferential edge surface with a diameter 873 so that as shown by the arrows in FIG. 8 saline can flow unimpeded through the lumens in each of center liner 843, inner insulator 847, and RF electrode 841.

An annular wall 841B of RF electrode 841 has an inner diameter so that annular portion 841B fits about and is affixed to inner insulator 847 by high temperature epoxy adhesive. In this example, the outer diameter of annular wall 841B is 0.070 in. However, this value is illustrative only. A length 877 of annular wall 841B is selected to facilitate affixing the wire used to supply power to RF electrode 841 and to affix RF electrode 841 securely to RF plasma catheter 840. In this implementation, length 877 is 0.050 in.

Catheter shaft body 842 is formed as described above from thermoplastic tubing.

Figure 10:
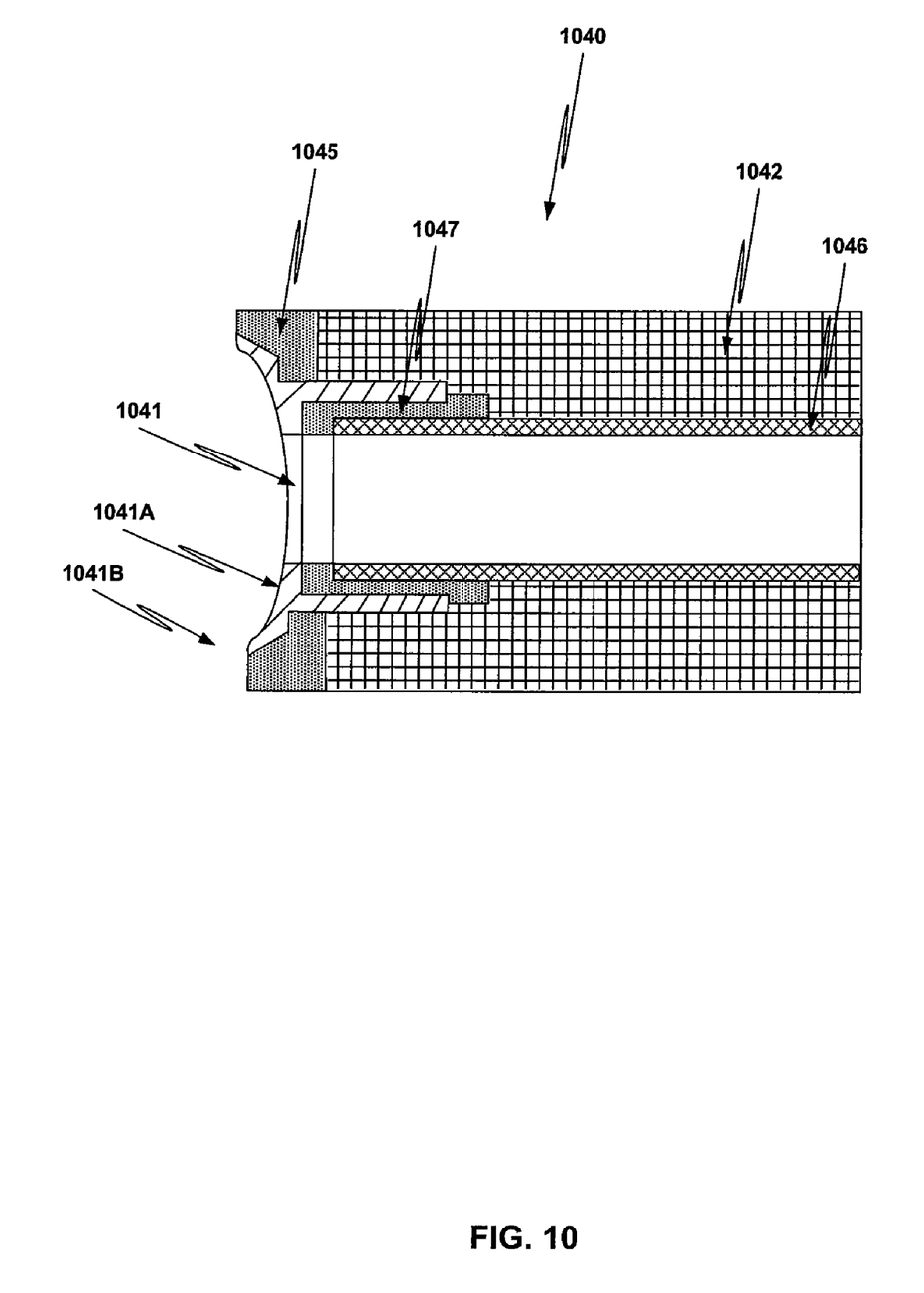
FIG. 10 is a cross-sectional view of one implementation of a RF plasma catheter that includes a RF electrode with a concave exterior edge surface and an outer insulator.

FIG. 10 is a cross sectional view of a portion of another implementation of a RF plasma catheter 1040 that includes an outer insulator 1045 which will maintain separation between a stent strut and the RF electrode. In this implementation, RF plasma catheter 1040 also includes RF electrode 1041, inner insulator 1047, center liner 1046, and catheter shaft body 1042. Outer insulator 1045, inner insulator 1047, center liner 1046, and catheter shaft body 1042 are equivalent to outer insulator 845, inner insulator 847, center liner 846, and catheter shaft body 1042, respectively as described above and so that description is incorporated herein by reference.

RF electrode 1041 is similar to RF electrode 841, expect the exterior edge surface is a combination of a concave exterior edge surface 1041A, which in this implementation is a smooth arc and an exterior ring edge surface 1041B. However, this is illustrative only and is not intended to limit the possible embodiments to this specific shape.

We claim:

1. A method comprising:
    starting a flow of a flush solution through a radiofrequency plasma catheter having a radiofrequency electrode located in a branch vessel blocked by a main stent graft located in a main vessel, wherein said main stent graft includes stent graft cloth;
    fenestrating in situ the main stent graft using the radiofrequency plasma catheter located in the branch vessel;
    wherein said fenestrating comprises applying power to said radiofrequency electrode of said radiofrequency plasma catheter at a time t1 after the starting of said flow;
    maintaining said flow of said flush solution during said applying power; and
    terminating said flow of said flush solution at a time t2 after said applying power is stopped.

2. The method of claim 1 further comprising:
    using an insulator of said radiofrequency plasma catheter to maintain a separation of said radiofrequency electrode from a strut of said main stent graft during said fenestrating.

3. The method of claim 1 wherein said flush solution comprises a saline solution.

4. The method of claim 1 wherein said flow of flush solution has a flow rate in a range from 50 ml/min to 100 ml/min.

5. The method of claim 1 wherein said flow of flush solution has a pressure in a range from 2 atmospheres to 15 atmospheres.

6. The method of claim 1 wherein said time t1 is about 50 milliseconds.

7. The method of claim 1 wherein said time t2 is about 50 milliseconds.

8. A method comprising:
    starting a flow of a flush solution through a radiofrequency plasma catheter having a radiofrequency electrode located in a branch vessel blocked by a main stent graft located in a main vessel, wherein said main stent graft includes stent graft cloth;
    creating a fenestration in said stent graft cloth by applying power to said radiofrequency electrode of said radiofrequency plasma catheter at a time t1 after the starting of said flow;
    maintaining said flow of said flush solution during said applying power; and
    terminating said flow of said flush solution at a time t2 after said applying power is stopped wherein said flow of said flush solution washes blood away from said radiofrequency electrode and thereby reduces coagulum formed by heating of blood associated with said applying power to said radiofrequency electrode.

9. The method of claim 8 further comprising:
    using an insulator of said radiofrequency plasma catheter to maintain a separation of said radiofrequency electrode from a strut of said main stent graft during said creating.

10. The method of claim 8 wherein said flush solution comprises a saline solution.

11. The method of claim 8 wherein said flow of flush solution has a flow rate in a range from 50 ml/min to 100 ml/min.

12. The method of claim 8 wherein said flow of flush solution has a pressure in a range from 2 atmospheres to 15 atmospheres.

13. The method of claim 8 wherein said time t1 is about 50 milliseconds.

14. The method of claim 8 wherein said time t2 is about 50 milliseconds.

15. The method of claim 8 further comprising:
    positioning said radio frequency electrode adjacent and in contact with said graft cloth prior to said creating.

* * * * *